(12) United States Patent
Wallen et al.

(10) Patent No.: US 6,450,968 B1
(45) Date of Patent: Sep. 17, 2002

(54) METHOD FOR DETERMINING GAS CONTENT IN A BREATHING APPARATUS, AND A BREATHING APPARATUS OPERATING ACCORDING TO THE METHOD

(75) Inventors: Lars Wallen, Spånga; Rolf Castor, Hägersten, both of (SE)

(73) Assignee: Siemens Elema AB, Solna (SE)

( * ) Notice: Subject to any disclaimer, the term of this patent is extended or adjusted under 35 U.S.C. 154(b) by 0 days.

(21) Appl. No.: 09/654,480

(22) Filed: Sep. 1, 2000

(30) Foreign Application Priority Data

Sep. 9, 1999 (SE) ................................................ 9903192

(51) Int. Cl.[7] ................................................. A61B 5/00
(52) U.S. Cl. ........................... 600/532; 73/23.3; 422/84
(58) Field of Search ................................. 600/529–538; 73/23.3; 422/84

(56) References Cited

U.S. PATENT DOCUMENTS

| | | | | |
|---|---|---|---|---|
| 3,946,228 A | * | 3/1976 | Biermann | 250/282 |
| 5,627,323 A | * | 5/1997 | Stern | 73/24.06 |
| 6,179,784 B1 | * | 1/2001 | Daniels et al. | 600/532 |

* cited by examiner

*Primary Examiner*—Robert L. Nasser
(74) *Attorney, Agent, or Firm*—Schiff Hardin & Waite

(57) ABSTRACT

In a method for determining the gas content, e.g. of oxygen in breathing gas in a breathing apparatus, and a breathing apparatus operating according to the method, the gas content is determined from the speed of sound in the breathing gas. In order to resolve the problems caused by temperature variations in gas samples, determination of the speed of sound is synchronized with one or more specific times in a respiratory cycle. Determination can then be made when conditions are most stable.

16 Claims, 2 Drawing Sheets

METHOD FOR DETERMINING GAS CONTENT IN A BREATHING APPARATUS, AND A BREATHING APPARATUS OPERATING ACCORDING TO THE METHOD

BACKGROUND OF THE INVENTION

1. Field of the Invention

The present invention relates to a method for determining the gas content in a breathing apparatus as well as to a breathing apparatus operating according to the method.

2. Description of the Prior Art

Accurate regulation of the oxygen content of breathing gas supplied to a patient with a breathing device is vitally important. Oxygen content is measured by an oxygen meter to ensure that the delivered oxygen content is correct. If the oxygen content of expired gas is also measured, the patient's consumption of oxygen can be established. Important information can also be derived from the amount of expired carbon dioxide. In other contexts, determination and monitoring of the concentration of other gases supplied, such as helium, also may be desirable.

One known method for determining the content of a gas component in a binary gas mixture (e.g. the oxygen content of a mixture of air and oxygen) involves determination of the speed of sound in the mixture. The speed of sound is usually measured with ultrasound, however, this type of measurement is temperature-related, since the speed of sound is temperature-related. The temperature of the mixture therefore is usually measured as well (or the temperature in a test chamber and test sample is regulated in such a way that a known temperature is maintained.)

Temperature variation is one problem encountered in the use of an ultrasonic-type gas meter in breathing apparatuses. The oxygen content of delivered breathing gas should be measured in every respiratory cycle. During inspiration, gas flows through the inspiration line at high speed for a relatively brief period. Temperature variations are therefore very striking and pose difficulties in simultaneous determination of temperature and air speed in an accurate and reliable manner.

SUMMARY OF THE INVENTION

An object of the present invention is to provide a method for determining the gas content of breathing gas in breathing devices which avoids the aforesaid problems.

Another object of the invention is to provide a breathing apparatus in which correct measurement of the gas content of breathing gas can be made.

The above object is achieved in accordance with the principles of the present invention in a method for determining a gas content in a breathing apparatus, and in a breathing apparatus operating according to the method, wherein the gas content is determined from the speed of sound in the gas, and wherein the determination of the speed of sound is synchronized with one or more specific times in a respiratory cycle.

By synchronizing measurements of the speed of sound with specific times in respiratory cycles, measurement can be made when the temperature is stable and easy to measure/monitor.

Performing the measurement immediately before an inspiration commences is particularly advantageous in the determination of the gas content of breathing gas for delivery to a patient. Conditions in the inspiration section of the breathing apparatus are then most stable. The fact that this causes a de facto one-breath lag in measurement of e.g. oxygen content does not pose any risk to the patient. At worst, she/he only receives one breath with a (partially) erroneous gas composition.

In a corresponding manner, the gas content in expired air can be determined by measurement before an expiration phase begins. Measurement of the content of both inspired and expired gas supplies information on the patient's uptake. Compensation must be made in this measurement, however, for the patient's contribution of carbon dioxide to the gas mixture. This is easily achieved with a carbon dioxide meter installed next to the oxygen meter.

Measurement can be made by pulsing ultrasound at a certain clock frequency in order obtain a series of measurement values at every determination of oxygen content. The measurement values can be used for identifying a trend.

If the trend is stable (the same results are obtained at every measurement point), the determined oxygen content can be accepted as correct.

If the trend is unstable, i.e. measurement values vary, the oxygen content can still be estimated by analyzing the measurement values. Exponential regression is a known method for such an analysis. It yields a sufficiently accurate approximation of oxygen content.

In an embodiment of the apparatus, the oxygen meter incorporates a measurement chamber with an inlet and outlet connected to an inspiration line. The inlet and outlet are equipped with sintered filters, causing heat to be stored, so the temperature in the measurement chamber is kept more constant. A slight drop in pressure, large enough to divert part of the flow during inspiration into the measurement chamber to replace the gas sample, is created with the aid of a mesh in the inspiration line.

In an alternative embodiment, valves are placed at the inlet and the outlet to control the exchange of gas samples.

DESCRIPTION OF THE PREFERRED EMBODIMENTS

Figure 1:
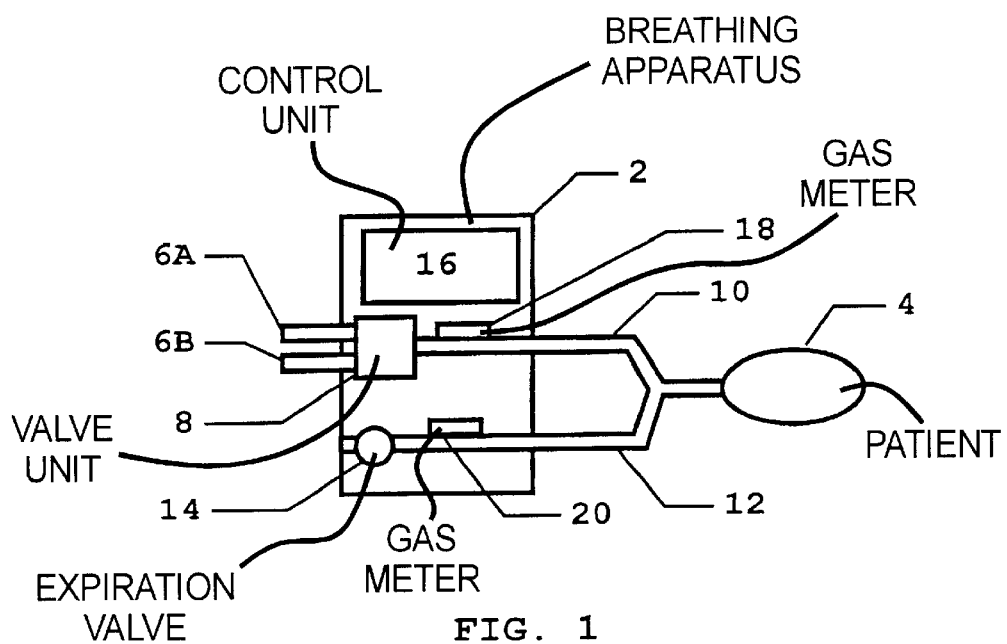
FIG. 1 shows an embodiment of a breathing apparatus according to the invention.

FIG. 1 shows a breathing apparatus 2 connected to a patient 4 in order to supply her/him with a breathing gas. The breathing gas is delivered to the breathing apparatus through a first gas connection 6A for air and a second gas connection 6B for oxygen. The proportions of air and oxygen are regulated in a valve unit 8 according to a pre-set oxygen concentration (21% to 100%). The valve unit 8 also regulates the pressure and flow of the breathing gas.

Other gases can naturally be connected to the breathing apparatus 2, e.g. oxygen-helium, air-carbon dioxide, etc.

The breathing gas is carried to the patient 4 in an inspiration line 10 and evacuated from the patient 4 in an expiration line 12. Here, an expiration valve 14 regulates e.g. end-expiratory pressure (PEEP) etc.

All functions in the breathing apparatus 2 are controlled by a control unit 16 in the known fashion. Here, the breathing apparatus 2 can be e.g. a Servo Ventilator 300 from Siemens-Elema AB, Sweden.

A first gas meter 18 is connected to the inspiration line 10 for determining the oxygen content of supplied breathing gas. A second gas meter 20 can be connected to the expiration line 12 for determining the content of expired gas. The gas meters 18, 20 can be oxygen meters for the air-oxygen gas mixture. For other gas mixtures, e.g. oxygen-helium, the gas meters 18, 20 can be helium meters. The measurement principle is the same, regardless of the gas mixture, thus the method is described below for measurement of oxygen.

Figure 2:
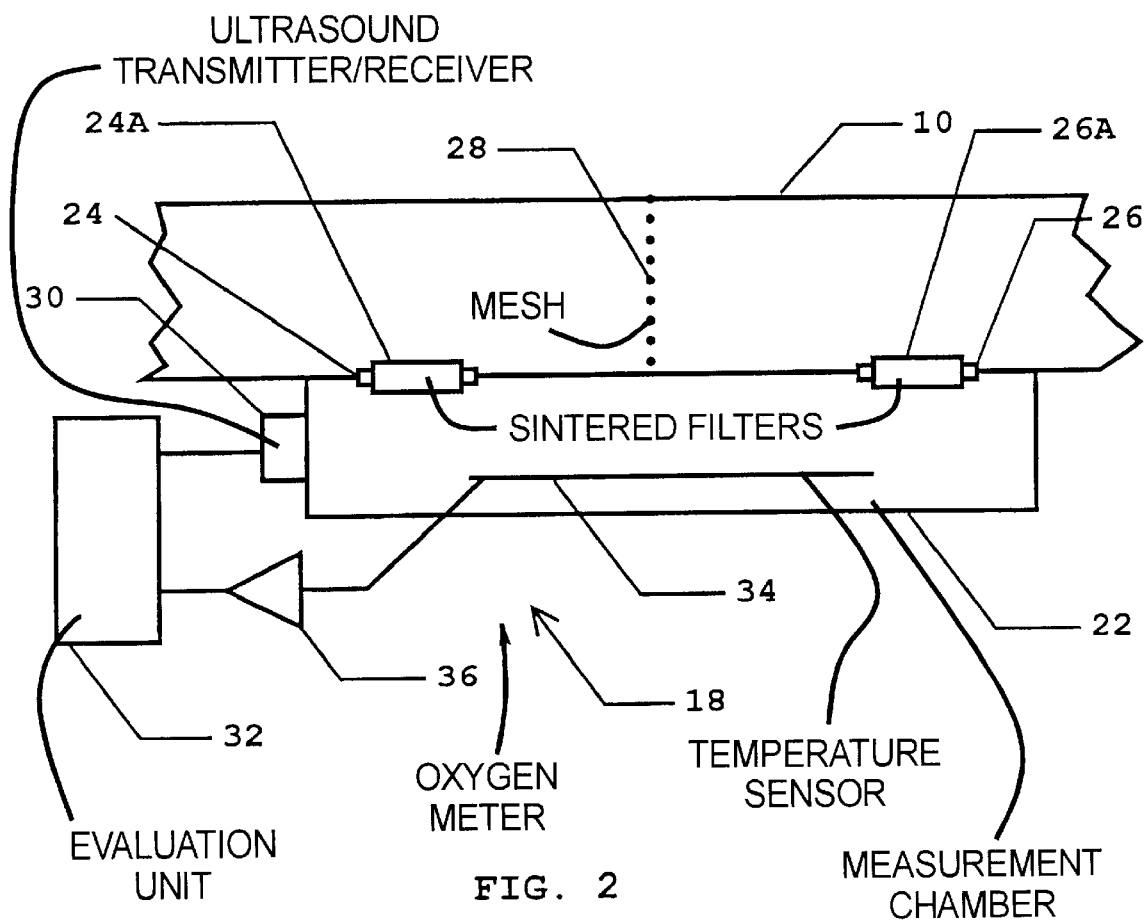
FIG. 2 shows a first embodiment of an oxygen meter in the inventive breathing apparatus.

FIG. 2 shows an embodiment of the first oxygen meter 18. The first oxygen meter 18 contains a measurement chamber 22 that is parallel to the inspiration line 10. A gas sample can be sent to the measurement chamber 22 through an inlet 24 which is, in this case, an orifice in which a first sintered filter 24A is arranged. The gas sample leaves the measurement chamber 22 through an outlet 26 consisting, in this case, of an orifice in which a second sintered filter 26A is arranged.

The gas sample in the measurement chamber is replaced at every inspiration. This is accomplished when a mesh 28 (or some other resistance) is arranged in the inspiration line 10 between the inlet 24 and the outlet 26. Pressure across the mesh 28 drops when breathing gas flows through the inspiration line 10. This diverts a small part of the inspiration flow into the inlet 24 (at the same time as the previous gas sample departs from the measurement chamber 22 through the outlet 26).

An ultrasonic transmitter/receiver 30 is arranged in the measurement chamber for measuring the speed of sound in the gas sample in the measurement chamber 22. The sound is emitted by the ultrasonic transmitter/receiver 30, bounces off the opposite wall of the measurement chamber 22 and returns to the ultrasonic transmitter/receiver 30. The speed of sound is determined in an evaluation unit 32. When measurements are to be made, the speed of sound can be determined e.g. every millisecond throughout the measurement procedure. This yields a series of measurement results all of which should be identical.

The speed of sound in the binary gas mixture of air and oxygen is related to the proportions of the two gases. Therefore, the composition (primarily the oxygen content) can be established by determining the speed of sound in the gas sample.

A temperature sensor 34 for determining the temperature is also arranged in the measurement chamber 22. Temperature information is sent, via an amplifier 36, to the evaluation unit 32. In the determination of the speed of sound (and accordingly the oxygen content) the prevailing temperature is taken into account.

Measurement of the oxygen content is made immediately before the inspiration phase begins in order to obtain the best possible measurement results. At that point, the temperature of the gas sample and the thermal sensor 34 have had the maximum time to stabilize.

This poses no problems in controlled respiration in which the inspiration phases are activated by the breathing apparatus 2. In supported respiration or spontaneous respiration, the start of the inspiration phase can be estimated from previous respiratory cycles. Alternatively, measurement can be made with somewhat wider margins and performed in the final phase of expiration, e.g. when flow in the expiration line 12 has dropped to a specific level. Other ways of determining a time before the inspiration phase are also conceivable.

As noted above, a number of measurements of the speed of sound (and accordingly oxygen content) can be made on each determination occasion (respiratory cycle). Measurement values can be used for establishing a trend.

As long as the trend is stable (oxygen content is constant for each measurement value with only a small percentage of deviating measurements), the measurement value can be accepted as a true value.

If the trend is unstable (the oxygen content varies in each measurement value), this may be indicate that conditions have not had time to stabilize properly. In principle, this measurement sequence can be ignored and a new measurement made in the next respiratory cycle.

It is also possible to approximate the true oxygen content from a trend analysis of the data obtained.

Figure 3:
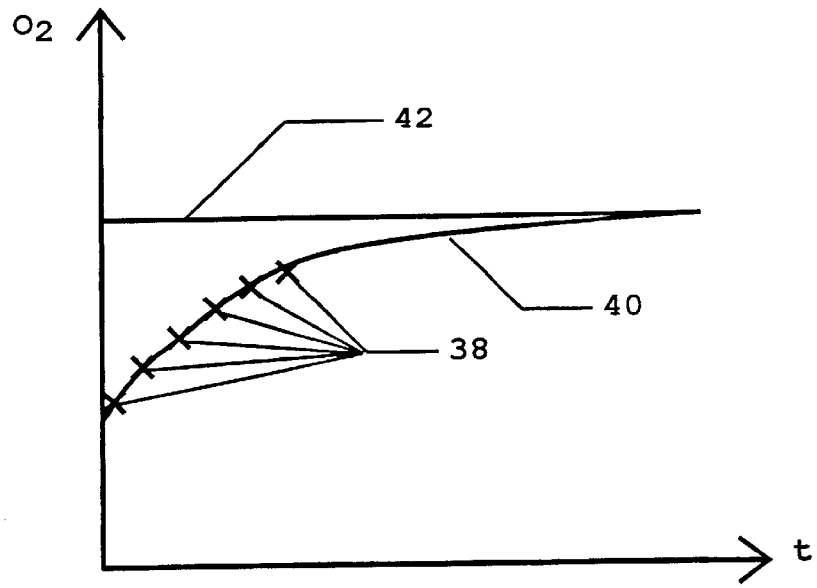
FIG. 3 is a diagram for estimating oxygen content in an embodiment of the method according to the invention.

One such trend analysis is illustrated in FIG. 3, a diagram showing oxygen content and time (measurement point). A few measurement points 38 have been shown in FIG. 3 to illustrate estimation of the true value for oxygen content. In principle, the distance between each measurement point 38 can be about 1 millisecond.

Using e.g. exponential regression, a curve 40 can be established for the measurement values. The curve 40 asymptotically approaches a line 42 used as an approximated value for the true oxygen content.

Figure 4:
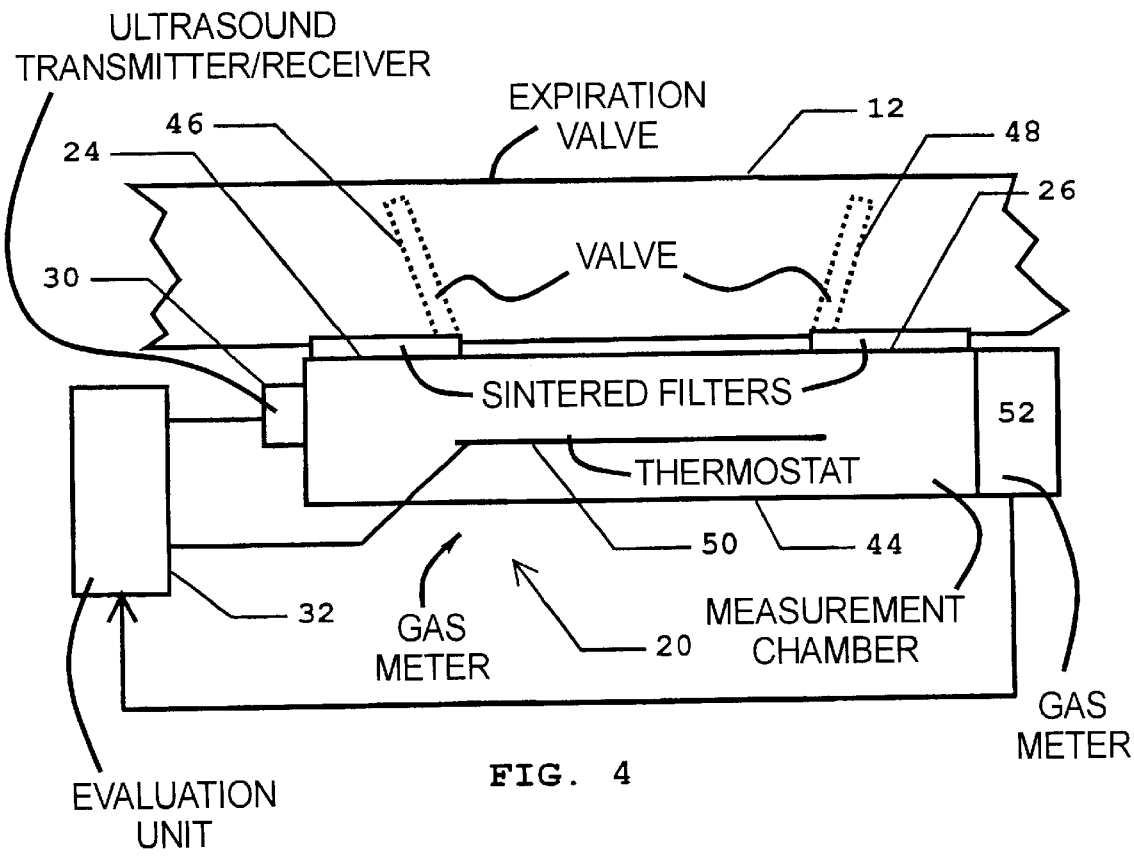
FIG. 4 shows a second embodiment of an oxygen meter in the inventive breathing apparatus.

A second embodiment of the gas meter is shown in FIG. 4. In this case, the gas meter 20 connected to the expiration line 12 is shown. The gas meter 20 has an elongated measurement chamber 44 arranged alongside the expiration line 12. Via a first valve 46 and a second valve 48 gas sample within the chamber 44 can be replaced by opening the valves 46, 48 as indicated with dotted lines. Preferably, the valves are constructed, so that essentially the entire flow in the expiration line 12 will pass through the chamber 44. By selecting the time when the valves are open, the gas sample obtained can be taken from any part of the breathing cycle. In the present embodiment, a gas sample for instance could be taken from the first part of expiration or from a latter part of the expiration. The valves 46, 48 need only be open as long as it takes to exchange the gas sample within the chamber 44.

A thermostat 50 is arranged within the chamber to provide a constant temperature on the sample. It may be preferable to have a temperature close to the gas samples temperature in order to speed up the time it takes to reach a uniform temperature in the chamber 44.

As in the first embodiment, an ultrasonic transmitter/receiver 30 is arranged in the chamber 44 for measuring the speed of sound in the gas sample and the evaluation unit 32 determines gas content.

In the second embodiment, the determination unit 32 could also include control means to control the valves 46, 48 (not shown in the figure). In the alternative, the valves can be controlled by a separate control unit or other means of control, dependent on the breathing cycles.

Since measurement in the second embodiment is made on a gas mixture that can contain three gases (for instance oxygen, nitrogen and carbon dioxide), a further measurement is required to make accurate calculations of e.g. oxygen content. A further gas meter 52 is arranged in or connected to the chamber 44. In this case, the further gas meter 52 measures content of carbon dioxide. A measurement signal indicating content of carbon dioxide is sent to the determination unit 32. The determination of gas content based on ultrasound is then compensated with known content of carbon dioxide.

Other versions of the aforementioned exemplifying embodiments are also conceivable. The gas meter according to the first embodiment can be used to measure gas content on the expiration side and the gas meter according to the second embodiment can be used to determine gas content on the inspiration side. Moreover, many combinations of the two embodiments are possible. For example, the temperature sensor 34 can be replaced with a thermostat 50 for maintaining a constant temperature in the measurement chamber. The sintered filters 24A, 26A can be replaced with other kinds of filters or left out altogether. The sintered filters 24A, 26A can also be used in combination with the valves 46, 48 in order to more rapidly achieve a stable environment in the measurement chamber 22,44. The important feature of the invention is synchronization of the determination of gas component content with specific times in respiratory cycles.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for determining a gas content of a gas component of breathing gas in a breathing apparatus, comprising the steps of:

connecting a breathing apparatus to a patient exhibiting a respiratory cycle;

making at least one measurement of a speed of sound in said breathing gas and determining a gas content in said breathing gas from the speed of sound therein; and synchronizing measurement of the speed of sound in said breathing gas with at least one predetermined time in said respiratory cycle.

2. A method as claimed in claim 1 comprising measuring the speed of sound in the breathing gas within a specific interval preceding an inspiration phase in said respiratory cycle.

3. A method as claimed in claim 1 comprising measuring the speed of sound in the breathing gas within a specific interval preceding an expiration phase in said respiratory cycle.

4. A method as claimed in claim 1 comprising measuring the speed of sound in the breathing gas a plurality of times to obtain a plurality of speed of sound measurements, and comparing said plurality of speed of sound measurements to determine a trend of said gas content.

5. A method as claimed in claim 4 comprising accepting said determination of said gas content from said plurality of measurements of the speed of sound in said breathing gas, if said trend is stable.

6. A method as claimed in claim 4 comprising approximating said gas content in said breathing gas from said plurality of measurements of the speed of sound in said breathing gas if said trend is not stable.

7. A method as claimed in claim 6 comprising approximating said gas content by exponential regression.

8. A breathing apparatus comprising:

an inspiration line and an expiration line adapted for connection to a patient exhibiting a respiratory cycle wherein breathing gas is adapted to be carried to a patient through said inspiration line during an inspiration phase of said respiratory cycle and wherein breathing gas is conducted away from a patient through said expiration line during an expiration phase of said respiratory cycle; and a gas meter in fluid communication with at least one of said inspiration line and said expiration line for determining a gas content of at least one gas component in said breathing gas, said gas meter determining a speed of sound in said breathing gas synchronized with at least one predetermined time in said respiratory cycle.

9. A breathing apparatus as claimed in claim 8 wherein said gas meter comprises an elongated measurement chamber having an inlet and an outlet both connected to said inspiration line and an ultrasound mete, for ultrasonically measuring the speed of sound in said inspiration line, a temperature unit for determining a temperature of said breathing gas in said inspiration line, and an evaluation unit supplied with the speed of sound from said ultrasound meter and with the temperature from said temperature unit for determining said gas content from said speed of sound and from said temperature.

10. A breathing apparatus as claimed in claim 9 wherein said gas meter comprises a first sintered filter disposed at said inlet and a second sintered filter disposed at said outlet, and a mesh disposed in said inspiration line between said first sintered filter and said second sintered filter.

11. A breathing apparatus as claimed in claim 9 wherein said gas meter comprises a first valve disposed at said inlet and a second valve disposed at said outlet for controlling a flow of said breathing gas through said measurement chamber.

12. A breathing apparatus as claimed in claim 9 comprising a second gas meter disposed in said inspiration line for measuring a further gas component in said breathing gas in said inspiration line, said second gas meter being connected to said evaluation unit.

13. A breathing apparatus as claimed in claim 8 wherein said gas meter comprises an elongated measurement chamber having an inlet and an outlet both connected to said expiration line and an ultrasound meter for ultrasonically measuring the speed of sound in said expiration line, a temperature unit for determining a temperature of said breathing gas in said expiration line, and an evaluation unit supplied with the speed of sound from said ultrasound meter and with the temperature from said temperature unit for determining said gas content from said speed of sound and from said temperature.

14. A breathing apparatus as claimed in claim 13 wherein said gas meter comprises a first sintered filter disposed at said inlet and a second sintered filter disposed at said outlet, and a mesh disposed in said expiration line between said first sintered filter and said second sintered filter.

15. A breathing apparatus as claimed in claim 13 wherein said gas meter comprises a first valve disposed at said inlet and a second valve disposed at said outlet for controlling a flow of said breathing gas through said measurement chamber.

16. A breathing apparatus as claimed in claim 13 comprising a second gas meter disposed in said expiration line for measuring a further gas component in said breathing gas in said expiration line, said second gas meter being connected to said evaluation unit.

* * * * *